(12) United States Patent
Haddadi et al.

(10) Patent No.: US 9,195,078 B2
(45) Date of Patent: Nov. 24, 2015

(54) METHOD FOR DETERMINING, IN A NATURAL POSTURE, AT LEAST ONE GEOMETRIC/PHYSIOGNOMIC PARAMETER ASSOCIATED WITH THE MOUNTING OF AN OPHTHALMIC LENS IN A SPECTACLE FRAME

(75) Inventors: Ahmed Haddadi, Charenton-le-Pont (FR); Jean Delzers, Charenton-le-Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 0 days.

(21) Appl. No.: 13/985,117

(22) PCT Filed: Dec. 30, 2011

(86) PCT No.: PCT/FR2011/000687
§ 371 (c)(1),
(2), (4) Date: Aug. 13, 2013

(87) PCT Pub. No.: WO2012/113994
PCT Pub. Date: Aug. 30, 2012

(65) Prior Publication Data
US 2013/0321763 A1    Dec. 5, 2013

(30) Foreign Application Priority Data

Feb. 21, 2011 (FR) ..................................... 11 00511

(51) Int. Cl.
*G02C 13/00* (2006.01)
*A61B 3/11* (2006.01)

(52) U.S. Cl.
CPC ................ *G02C 13/005* (2013.01); *A61B 3/11* (2013.01)

(58) Field of Classification Search
CPC ... A61B 3/0058; G02C 13/003; G02C 13/005
USPC .......................................................... 351/204
See application file for complete search history.

(56) References Cited

U.S. PATENT DOCUMENTS 7,950,800 B2   5/2011   Nauche et al.
8,360,580 B2   1/2013   Chauveau
(Continued)

FOREIGN PATENT DOCUMENTS

FR        2 914 173     10/2008
FR        2 915 290     10/2008
WO        2006/029875    3/2006
(Continued)

OTHER PUBLICATIONS

International Search Report dated Mar. 27, 2012, corresponding to PCT/FR2011/000687.

*Primary Examiner* — Jordan Schwartz
(74) *Attorney, Agent, or Firm* — Young & Thompson

(57) ABSTRACT

Method for determining, in a natural posture, at least one geometric/physiognomic parameter associated with the mounting of an ophthalmic lens in a spectacle frame intended to be worn by a wearer. The method includes: (a) capturing at least one substantially frontal image of the wearer's head; (b) determining a measured value of an angle of inclination during the capturing step, which depends on the inclination of the wearer's head about a main axis perpendicular to a sagittal plane of the wearer's head; (c) determining a reference value of the angle of inclination corresponding to a natural posture of the wearer's head; and (d) determining the required geometric/physiognomic parameter on the basis of the substantially frontal image captured and as a function of the difference between the measured value of the angle of inclination determined in step (b) and the reference value of the angle of inclination determined in step (c).

19 Claims, 4 Drawing Sheets

(56) References Cited

U.S. PATENT DOCUMENTS

Figure 1:
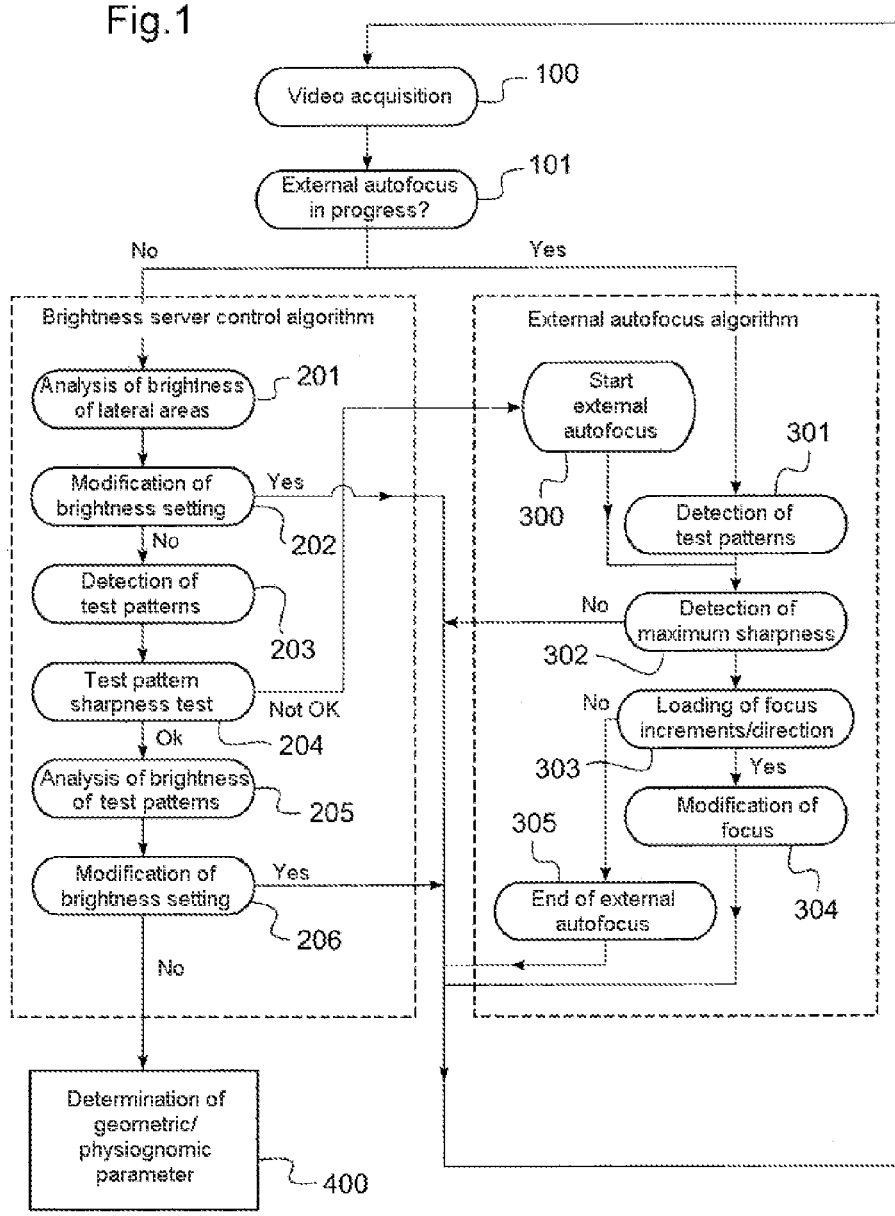

2012/0033178 A1* 2/2012 Chauveau et al. ............ 351/204
2012/0182521 A1* 7/2012 Kubitza et al. ................ 351/204

FOREIGN PATENT DOCUMENTS

| WO | 2009/024681 | 2/2009 |
| WO | 2010/119190 | 10/2010 |

* cited by examiner

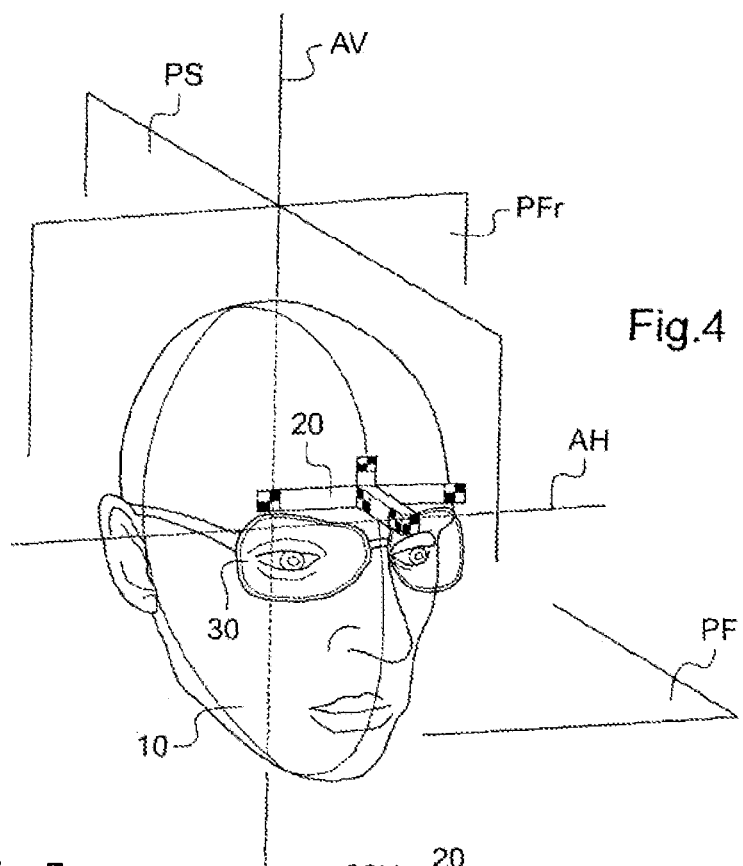
Fig.4
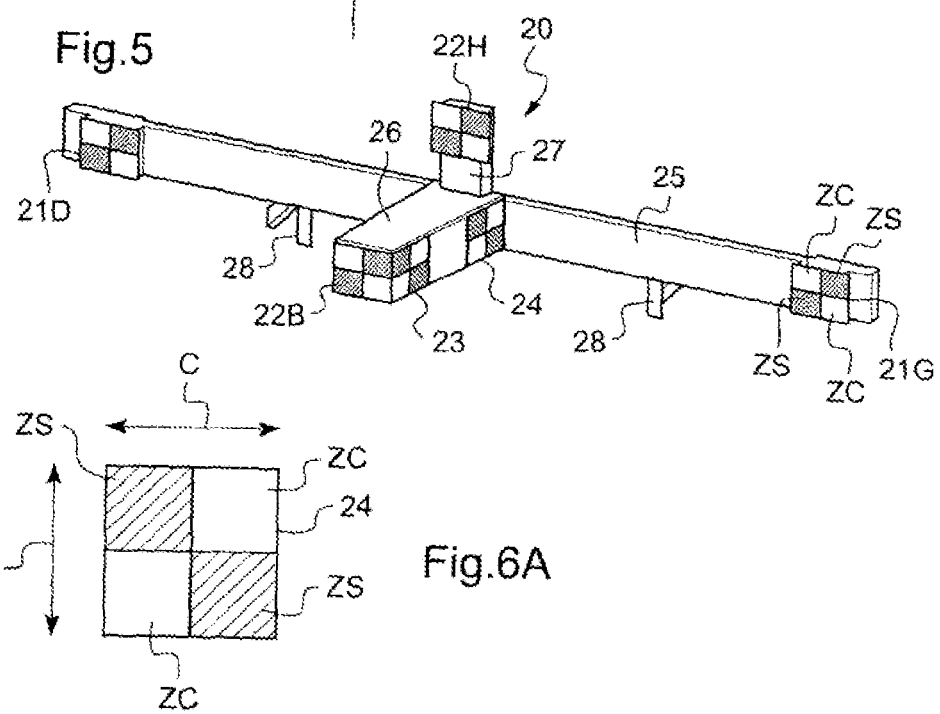
Fig.5
Fig.6A

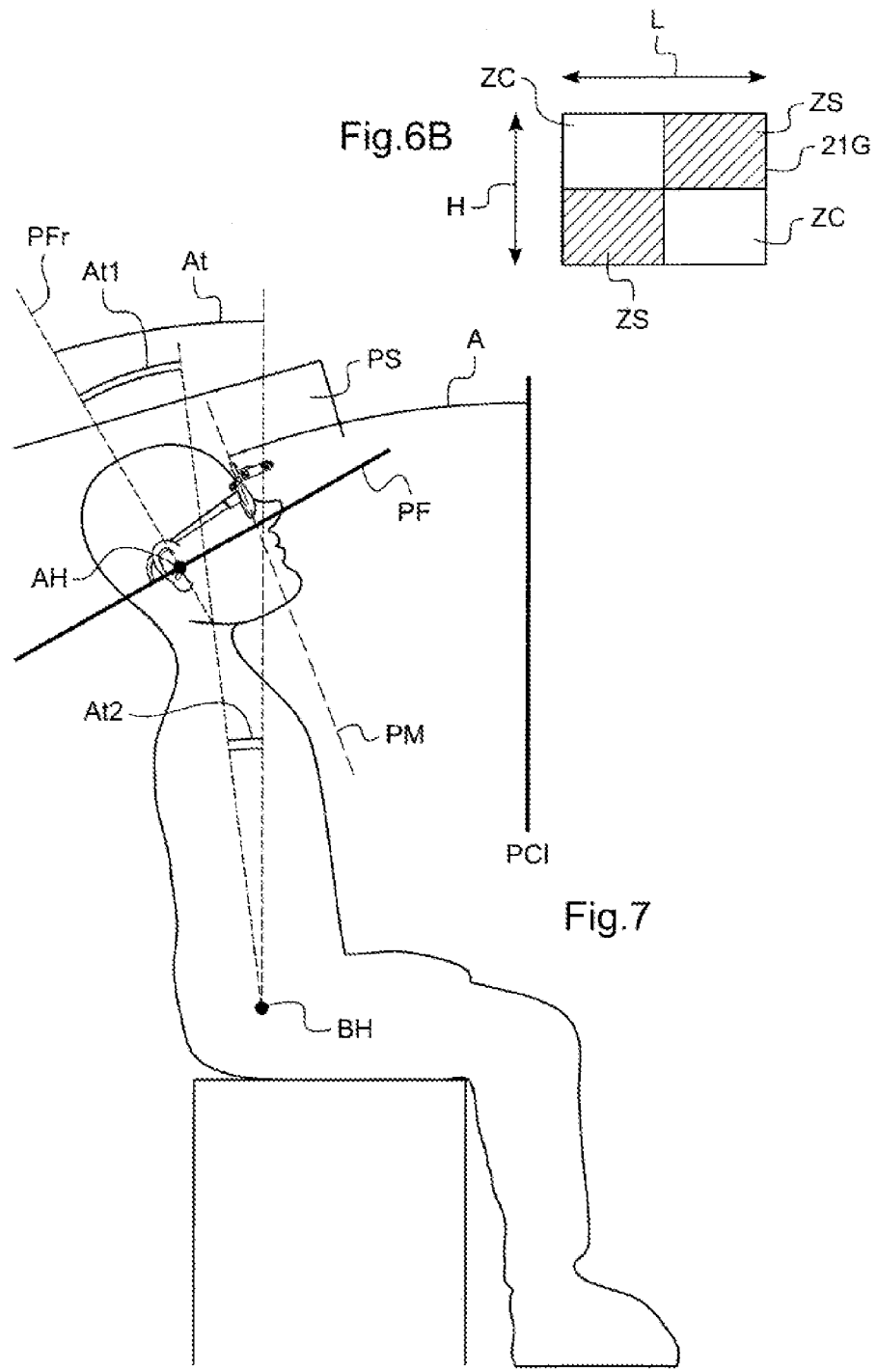

METHOD FOR DETERMINING, IN A NATURAL POSTURE, AT LEAST ONE GEOMETRIC/PHYSIOGNOMIC PARAMETER ASSOCIATED WITH THE MOUNTING OF AN OPHTHALMIC LENS IN A SPECTACLE FRAME

TECHNICAL FIELD TO WHICH THE INVENTION RELATES

The present invention relates generally to a method for determining at least one geometric/physiognomic parameter associated with the mounting of an ophthalmic lens in a spectacle frame worn by a wearer.

TECHNOLOGICAL BACKGROUND

Making a corrective lens for spectacles comprises, on the one hand, the optical design and shaping of the refractive faces of the lens and, on the other hand, the adaptation of the lens to the selected spectacle frame.

The present invention deals with the measurement, on the face of the wearer, of geometric/physiognomic parameters that give an account of the positioning configuration of the spectacles on the face of the wearer. These parameters are likely to be used in the two steps of making a corrective lens, in order for the lens to ultimately provide the corrective optical function for which it was designed and prescribed. They are notably the interpupillary distance, the height of the pupils of the eyes of the wearer relative to the bottom edge of the frame, and/or the pantoscopic angle formed by the general plane of the frame or of the lens relative to the vertical.

The looked-for geometric/physiognomic parameters are linked both to the geometry of the head of the wearer and the selected spectacle frame, as well as to the posture of the wearer.

As is known, it is possible to determine these parameters manually. For example, the measurement of the height of the eyes of the wearer relative to the bottom edge of the frame can be performed by the optician who observes the wearer from the front and makes a rough measurement, by means of a rule, of the distance between the pupil of an eye and the bottom edge of the presentation lens.

These parameters can also be determined from one or more captured images of the wearer's head.

However, whether manual or computerized, these methods for determining geometric/physiognomic parameters of the wearer suffer from a great inaccuracy. In practice, to perform an accurate measurement by rule or by processing captured images, it is necessary for the wearer's head to be in its natural posture at the time of the measurement or of the image capture.

This natural posture is also called anatomical posture or orthostatic position. In this natural posture, which will be defined in more detail later, the wearer holds his or her head straight and looks toward the distance, toward the horizon.

For reasons of speed of execution and comfort for the optician as for the wearer, the position of the wearer's head when the image is taken is not imposed.

However, even if the position of the wearer's head is not imposed, the wearer is not usually in the natural posture while the geometric/physiognomic parameters are being determined.

This is because the application of these methods for determining the geometric/physiognomic parameters entails bringing a measuring apparatus close, generally to less than a meter, to the wearer. The optician is also close in the case of a manual measurement.

The wearer then looks at this measuring apparatus or the optician who is then located in front of him or her during the measurement.

The proximity of the apparatus or of the optician causes the wearer, in practice, to bend slightly backward.

The wearer is then in a strained and unnatural posture. His or her gaze is not directed straight in front, to the horizon, but fixed on a close object.

Now, a deviation of 1 degree of inclination of the head in its sagittal plane relative to the anatomical posture introduces an error of 1 degree on the measurement of the pantoscopic angle and an error of 0.5 millimeter on the measurement of the heights of the eyes.

Moreover, determining said geometric/physiognomic parameters from captured images entails identifying, on the captured image, the image of at least one indexing element positioned on the face of the wearer and having at least one predetermined geometric characteristic.

It is then possible to determine the looked-for geometric/physiognomic parameter by comparing the geometric characteristic of the image of the indexing element and its corresponding real geometric characteristic.

However, such a method can be implemented only if the identification of the indexing elements on the captured image is possible.

This is not notably the case if the captured image is blurred or if it is overexposed or underexposed to the point that the image of the indexing elements cannot be identified.

In particular, when an image is captured using a device comprising a means for automatically setting the focal distance of acquisition of the image, it is possible that the image capture device will focus on a point of the image that does not form part of the wearer's head, which means that the wearer's head appears blurred on the captured image. Furthermore, when the wearer is positioned backlit relative to the image capture device, the captured image is often too dark to allow the image of the indexing element to be identified.

One solution to these various problems consists in manually setting the sharpness and the brightness of the captured image before each image capture. However, this presents the drawback of being long and tedious for the optician. Furthermore, it is not feasible in the context of continuous image acquisition in video mode.

OBJECT OF THE INVENTION

In order to remedy the abovementioned drawbacks of the prior art, the present invention proposes a method for determining geometric/physiognomic parameters of a wearer in his or her natural position, whatever the brightness conditions during the image capture and whatever the position of the wearer's head in relation to the image capture device.

More particularly, there is proposed, according to the invention, a method for determining, in a natural posture, at least one geometric/physiognomic parameter associated with the mounting of an ophthalmic lens in a spectacle frame intended to be worn by a wearer, comprising the following steps:

a) capturing at least one substantially frontal image of the wearer's head, b) determining a measured value of an angle of inclination of the wearer's head, during the capture of the substantially frontal image, which depends on the inclination of the wearer's head about a main axis perpendicular to a sagittal plane of the wearer's head, c) determining a reference value of said angle of inclination corresponding to a natural posture of the wearer's head, and d) determining said looked-for geometric/physiognomic parameter on the basis of the substantially frontal image captured and as a function of the difference between said measured value of the angle of inclination determined in step b) and said reference value of said angle of inclination determined in step c).

Thus, the fact that the wearer's head is in a posture that is different from the natural posture during the capture of the image in step a) is taken into account in determining the looked-for parameter.

The difference between the real posture of the wearer during the image capture and the natural posture is assessed by the comparison between the measured real value of the angle of inclination during the capture of the substantially frontal image and a reference value of this angle of inclination corresponding to the natural posture of the wearer.

It is then possible to either correct the geometric characteristic measured on the image of the indexing element, or correct the geometric/physiognomic parameter determined on the basis of the uncorrected geometric characteristic of the indexing element to obtain the value of the looked-for geometric/physiognomic parameter in a natural posture.

Other nonlimiting and advantageous features of the method according to the invention are as follows:

in step b), the angle of inclination is the angle formed between a plane integral with the wearer's head and an image capture plane associated with the capture of said substantially frontal image;

said plane integral with the wearer's head is a mean plane of the circles of the spectacle frame positioned on this wearer's head;

said angle of inclination of the wearer's head comprises a component linked to the rotation of the wearer's head about a first main axis of the wearer's head perpendicular to the sagittal plane of the wearer's head, which corresponds to a rotation of the wearer's head relative to his or her body, and/or a component linked to the rotation of the wearer's head about a second main axis perpendicular to the sagittal plane of the wearer's head, which corresponds to a rotation of the wearer's body about this second main axis;

the wearer's head comprises at least one frontal indexing element positioned in such a way that it is identifiable on said substantially frontal image of the face of the wearer, and, in step b):

b1) the image of the frontal indexing element is identified on this substantially frontal image, b2) a geometric characteristic of the image of this frontal indexing element is determined, b3) said measured value of the angle of inclination associated with the substantially frontal image is determined as a function of the geometric characteristic determined in step b2);

said frontal indexing element is a noteworthy anatomical element of the wearer's head;

said frontal indexing element is situated on an accessory positioned on the wearer's head;

in step c), the following steps are carried out:

c1) at least one substantially profile image of the wearer's head in a natural posture is captured, the wearer's head comprising at least one profile indexing element positioned in such a way that it is identifiable on said substantially profile image of the wearer's face, c2) on said substantially profile image, the image of this profile indexing element is identified, c3) a geometric characteristic of the image of this profile indexing element is determined, and c4) said reference value of said angle of inclination is determined as a function of the geometric characteristic determined in step c3);

steps c1) to c4) are repeated and the reference value of the angle of inclination is determined as the average value of the reference values determined in a plurality of steps c4) carried out;

the successive steps c1) are performed using an image capture device in video mode;

said profile indexing element is a noteworthy anatomical element of the wearer's head;

said profile indexing element is situated on an accessory positioned on the wearer's head;

the relative position of said frontal and profile indexing elements is predetermined and is used to determine the looked-for geometric/physiognomic parameter in step d);

the wearer's head also comprising at least one brightness calibration indexer comprising at least two contrasted areas, visible in said profile image of the wearer, the method also comprises the following steps, prior to step c):

e) a substantially profile image of the wearer's head is captured, f) a measured value of the brightness of at least a portion of the image of the calibration element captured in step e) is determined, g) a setting parameter of the optical image acquisition conditions of said image capture device is modified as a function of this measured value, so as to improve the contrast of the image of the contrasted areas of the calibration element;

in step g), g1) the deviation between the brightness value determined in step f) and a target brightness value is determined, g2) this deviation is compared with a predetermined maximum value of this deviation, g3) based on this comparison, the setting parameter of the optical acquisition conditions of the image capture device is modified so as to make said measured value tend toward said target brightness value;

in step c1), the substantially profile image of the wearer's head is captured with the setting parameter of the optical acquisition conditions modified in step g);

the method also comprises the following steps, prior to step c):

h) a substantially profile image of the wearer's head is captured, i) the position of the image of the profile indexing element on this image captured in step h) is determined, j) a sharpness parameter representative of the sharpness of the image of this profile indexing element on this image is determined, k) this sharpness parameter is compared with a predetermined sharpness threshold value, l) the image acquisition focal distance of said image capture device is modified as a function of the difference between the sharpness parameter determined in step j) and said sharpness threshold value, so as to improve the sharpness of the image of the profile indexing element;

in step h), the profile image of the wearer's head is captured with the setting parameter of the optical acquisition conditions modified in step g);

in step e), the profile image of the wearer's head is captured with the setting parameter of the optical acquisition conditions modified in step l);

in step c1), the profile image of the wearer's head is captured with the image acquisition focal distance modified in step l);

in step j), the size or the brightness of the image of a particular point of the profile indexing element is determined, and said sharpness parameter is deduced therefrom;

said profile brightness calibration element is merged with the profile indexing element;

in step b), said measured value of the angle of inclination of the head is measured using an inclinometer;

in step c), the reference value of the angle of inclination is extracted from a predetermined database;

in step c), the reference value of the angle of inclination of the head is measured using an inclinometer.

DETAILED DESCRIPTION OF AN EXEMPLARY EMBODIMENT

The description which follows below in light of the appended drawings, which are given as nonlimiting examples, will clearly show what the invention consists of and how it can be implemented.

Figure 2:
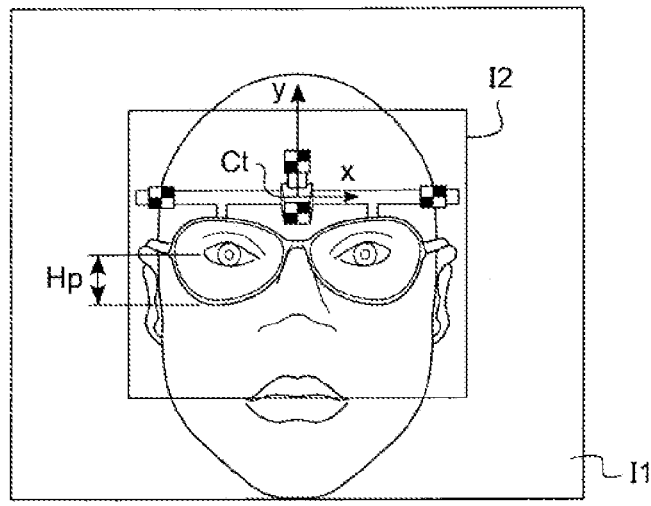
Figure 3:
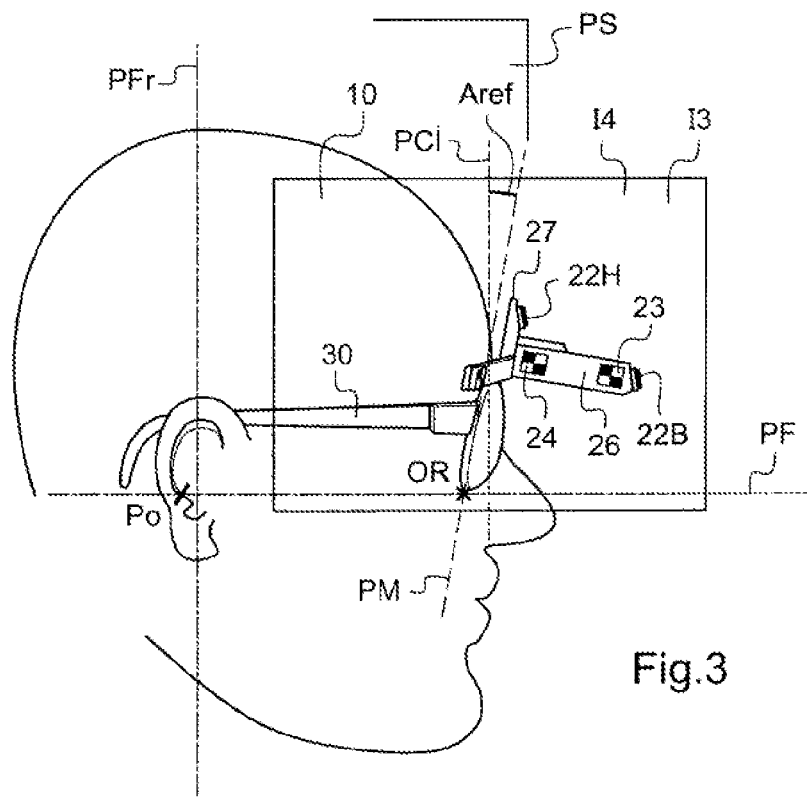

In the appended drawings:

FIG. 1 is a schematic diagram of the steps of one possible embodiment of the invention, FIG. 2 is a schematic view of a substantially frontal image captured by the image capture device, FIG. 3 is a schematic view of a substantially profile image captured by the image capture device, FIG. 4 is a schematic view of the wearer's head equipped with the lens frame and the accessory, FIG. 5 is a perspective schematic view of an accessory comprising visible frontal and profile indexing and calibration elements for implementing the method according to the invention, FIG. 6A is a front schematic view of an indexing and calibration element of the accessory of FIG. 5, which can be seen in a profile view of this accessory, and FIG. 6B is a front schematic view of an indexing and calibration element of the accessory of FIG. 5, visible in a front view of this accessory, FIG. 7 is a schematic profile view of the wearer during the image capture in step a).

Hereinbelow, the vertical direction is defined as that given by a plumb line and the horizontal direction is given as the direction perpendicular to this vertical direction.

FIG. 1 shows the steps of a possible embodiment of the method according to the invention.

The aim in implementing this method is to determine at least one geometric/physiognomic parameter associated with mounting an ophthalmic lens in a spectacle frame, in the natural posture of the wearer, such as, for example, the interpupillary distance, the height of the pupils of the eyes of the wearer relative to the bottom edge of the frame.

The method comprises the following steps, which are described hereinbelow in more detail:

a) capturing at least one substantially frontal image of the wearer's head, b) determining a measured value of an angle of inclination of the wearer's head during the capture of the substantial frontal image, which depends on the inclination of the wearer's head about a main axis perpendicular to a sagittal plane of the wearer's head, c) determining a reference value of said angle of inclination corresponding to a natural posture of the wearer's head, and d) determining said looked-for geometric/physiognomic parameter on the basis of the substantially frontal image captured and as a function of the difference between said measured value of the angle of inclination determined in step b) and said reference value of said angle of inclination determined in step c).

Step a)

At least one substantially frontal image of the wearer's head is captured.

FIG. 4 is a schematic view of the wearer's head 10 showing the position of its various noteworthy planes.

As represented in FIGS. 3 and 4, the Frankfurt plane PF of the wearer's head 10 is defined as the plane passing through the lower orbital points OR and the portion PO of the wearer, the portion being the highest point of the skull of the ear canal, which corresponds to the tragion of the ear.

When the wearer is in a natural posture, this Frankfurt plane PF is substantially horizontal.

Such is the case for example when the wearer is in a seated or standing configuration in which his or her head 10 is straight and he or she is looking straight in front, to the far distance, that is to say preferably to the horizon. The gaze axis of the wearer is then horizontal.

It is also said that the wearer assumes an orthostatic position, or a position in which he or she applies a minimum of efforts.

A sagittal plane PS of the wearer's head 10 is defined as being the plane perpendicular to the Frankfurt plane passing through the perpendicular bisector of the two eyes. The perpendicular bisector of the eyes is the axis passing through the middle of the segment defined by the centers of rotation of the two eyes and parallel to the Frankfurt plane PF.

A frontal plane PFr of the head is also defined as being a plane perpendicular to the Frankfurt plane and passing through the top of the head. This plane is also perpendicular to the sagittal plane PS.

In these conditions, a vertical axis AV of the head 10 is defined as the intersection of the frontal plane and of the sagittal plane and a horizontal axis AH of the head is defined as the intersection of the Frankfurt plane and the frontal plane.

This horizontal axis AH is therefore an axis perpendicular to the sagittal plane PS of the wearer's head.

A substantially frontal image then corresponds to an image for which the image capture plane of the image capture device forms an angle of between +20 and −20 degrees, about the vertical axis AV with the frontal plane PFr of the wearer's head.

A substantially profile image similarly corresponds to an image for which the image capture plane of the image capture device forms an angle of between +10 and −10 degrees about the vertical axis AV with the sagittal plane PS of the wearer's head.

An example of a substantially frontal image I1 is shown in FIG. 2. An example of a substantially profile image I3 is shown in FIG. 3.

Step b)

The angle of inclination A of the wearer's head for which a measured value is determined during the capture of the substantially frontal image depends on the inclination of the wearer's head about a main axis perpendicular to the sagittal plane of the wearer's head.

This main axis is, for example, here, the horizontal axis AH. The measured angle of inclination therefore corresponds to an angle of inclination in the sagittal plane PS of the wearer's head.

In practice, the measured value of this angle is, for example, determined on the basis of the substantially frontal image captured in step a).

The measured value of the angle formed between a plane integral with the wearer's head 10 and an image capture plane PCI associated with this image captured in step a) is, for example, determined.

The image capture plane PCI corresponds to the plane of the captured image.

The plane integral with the wearer's head 10 is preferentially a plane perpendicular to the sagittal plane PS of the wearer's head.

This angle corresponds more specifically to the angle between the intersection of this plane integral with the wearer's head and a plane perpendicular to the image capture plane and the intersection of the image capture plane and this plane perpendicular to said image capture plane.

The plane integral with the wearer's head 10 is, for example, the mean plane of the circles of the spectacle frame 30 worn by the wearer. In practice, when the wearer's head moves, the spectacle frame moves at the same time and the position of the mean plane PM of the circles of the frame relative to the wearer's head is unchanged.

As a variant, the plane integral with the head can be a particular plane of the head itself, for example the frontal plane PFr. It is preferentially a plane parallel to the horizontal axis AH of the wearer's head.

The angle of inclination A is represented in FIG. 7. The image capture plane PCI is here considered to be oriented vertically.

This angle of inclination A of the mean plane PM of the circles of the frame 30 varies in the same way as the angle At formed between the respective intersections of the frontal plane PFr of the wearer's head 10 and of the image capture plane PCI with the plane perpendicular to said image capture plane.

These two angles A and At are equal to within a constant.

As represented in FIG. 7, the angle At of the frontal plane PFr of the wearer's head relative to the image capture plane PCI here comprises a first component At1 (see FIG. 7) linked to the rotation of the frontal plane PFr of the wearer's head about the horizontal axis AH of the wearer's head corresponding to a rotation of the wearer's head relative to his or her body. The angle At of the frontal plane PFr of the wearer's head relative to the image capture plane PCI also comprises a second component At2 (see FIG. 7) linked to the rotation of the frontal plane PFr of the wearer's head 10 relative to a horizontal axis BH which is also perpendicular to the sagittal plane PS of the wearer's head. This second component corresponds to a rotation of the body of the wearer about this horizontal axis BH.

FIG. 7 shows the two components At1, At2 of the angle At of the frontal plane PFr in the interests of simplicity. It is obvious that the angle of inclination A of the mean plane PM of the circles of the frame of the wearer also comprises two similar components, since the inclination of the mean plane PM of the circles of the frame follows that of the head.

The wearer's head 10 preferentially comprises at least one frontal indexing element positioned in such a way that it can be identified in said substantially frontal image of the face of the wearer captured in step a).

This frontal indexing element can be a noteworthy anatomical element of the wearer's head, for example the pupil and/or the iris of one of the eyes, the contour of the eye, the wings of the nose of the wearer.

However, the frontal indexing element is preferably situated on an accessory positioned on the wearer's head.

It may, for example, be a self-adhesive sticker stuck to the wearer's head.

It is preferentially an accessory 20 as represented in FIG. 5 and intended to be mounted on the spectacle frame 30 of the wearer.

The accessory 20 comprises (FIG. 5) a main bar 25 suitable for positioning above the spectacle frame, in the mean plane PM of the circles of this frame.

The accessory 20 has, for this purpose, means for mounting on the frame 30 which here take the form of clips 28 extending from the main bar 25.

Two clips 28 are provided here, each suitable for being attached to one of the circles of the frame 30.

This accessory 20 also comprises a projection 26 extending perpendicularly to the main bar 25, in a plane substantially perpendicular to the mean plane PM of the circles of the frame when the accessory 20 is fixed onto this frame 30, and a protruding element 27 rising perpendicularly to the main bar 25 and to the projection 26, in the mean plane PM of the frame 30 or in a plane parallel to this mean plane PM when the accessory 20 is fixed onto this frame (FIG. 3).

Here, the accessory 20 comprises eight indexing elements 21D, 21G, 22H, 22B, 23, 24. Two indexing elements 21D, 21G are positioned at the ends of the main bar 25, and are oriented so as to be visible on a frontal image of the wearer, when the accessory 20 is fixed onto the frame of the wearer. These indexing elements are therefore frontal indexing elements of the wearer's head.

An indexing element 22H is positioned on the protruding element 27 and another indexing element 22B is positioned at the end of the projection 26, in such a way that these two indexing elements 22H, 22B are visible in a frontal image of the wearer. These indexing elements are therefore also frontal indexing elements of the wearer's head.

Furthermore, these two indexing elements 22H, 22B are positioned in such a way that, on a frontal image of the accessory, they are situated one below the other.

Finally, the lateral sides of the projection also each bear two indexing elements 23, 24 which are visible in the substantially profile images of the wearer, as explained in more detail later. These indexing elements are therefore profile indexing elements of the wearer's head.

Each frontal or profile indexing element has one or more predetermined geometric characteristics, for example its dimensions or the dimensions of a geometric pattern borne by it. The geometric pattern can, for example, take the form of a test pattern or alternating contrasted bands.

Each indexing element here comprises four contrasted areas ZS, ZC. These contrasted areas are positioned in alternation, each area forming a right angle with a common apex with the right angles formed by the other areas. Said common apex of the light and dark areas forms the center of the indexing element. These indexing elements are also called "test pattern", as is the case in FIG. 1 for example.

In practice, as represented in more detail in FIG. 6B for the frontal indexing element 21G, each frontal indexing element 21D, 21G, 22H, 22B, here takes the form of a rectangle of length L between 8 and 11 millimeters and of height H between 5 and 8 millimeters.

This rectangle is divided into four smaller rectangles of equal dimensions. In the smaller rectangles, the diagonally paired rectangles have identical luminances or colors, and the adjacent pairs of rectangles have different luminances or colors.

As a variant, said indexing elements can have any other form, notably square or circular.

As represented in more detail in FIG. 6A for the profile indexing element 24, the profile indexing elements 23, 24 are preferably square with a side length Ct equal to 6 millimeters. This square is divided into four smaller squares of equal dimensions. In the smaller squares, the diagonally paired squares have identical luminances or colors, and the adjacent pairs of squares have different luminances or colors.

As a variant, the frontal and profile indexing elements can have only two or three contrasted areas, for example a dark disc concentric with a lighter disc or vice versa, or two contrasted areas separated by a straight line, or even a light band between two dark bands for example. On the other hand, more than four contrasted areas can be provided, for example concentric contrasted rings or an alternation of light and dark bands.

In order to determine the measured value of the angle of inclination A, the following substeps are, for example, carried out:

b1) the image of the frontal indexing element is identified in the substantially frontal image captured in step a), b2) a geometric characteristic of the image of this frontal indexing element is determined, and b3) said angle of inclination A associated with the substantially frontal image is determined as a function of this geometric characteristic.

The steps b1) and b2) can be carried out manually by the operator or automatically by processing the image captured in step a).

One example of processing of the image captured in step a) making it possible to identify the image of each frontal indexing element in step b1) on the substantially frontal image will be given later.

From the position of the images of the indexing elements, it is possible to deduce the position of other noteworthy points of the image.

In particular, the position of a point Ct situated in the middle of the centers of the indexing elements 21D, 21G positioned at each end of the bar 25 of the accessory 20 (FIG. 2).

According to one possible processing example, in step b2), the coordinates of the centers of the images of the indexing elements on the captured image are determined, in a reference frame of the image.

In particular, the coordinates of the center of the frontal indexing element 22B situated at the end of the projection of the accessory is determined within this reference frame, as well as those of the point Ct defined previously. The length of the segment linking the center of the image of the indexing element 22B situated at the end of the projection and the point Ct on the image is deduced therefrom.

In a particular case where the image captured in step a) is captured at an instant where the horizontal axis AH of the head is parallel to the image capture plane PCI, preference is given to defining the reference frame of the image Ct(x,y) which has the point Ct for its origin and axes x and y extending respectively along the image of the bar 25 of the accessory and the image of the protruding element 27 of the accessory, as represented in FIG. 2.

In these conditions, the looked-for segment length is equal to the coordinate yb on the axis y from the center of the indexing element 22B.

The distance Db that in reality exists between the indexing element 22B situated on the projection and the point Ct of the accessory 20 is also known by construction of the accessory 20.

The distance Db that exists between the indexing element 22B situated on the projection and the point Ct of the accessory 20 is known by construction.

The measured value Am of the angle of inclination A on the image is then deduced therefrom by the formula: $Am=\arcsin(yb/Db)$, where arcsin is the inverse function of the sine function.

As a variant, in step b), said measured value of the angle of inclination of the head is measured using an inclinometer.

Step c)

A reference value of the angle of inclination, which corresponds to the value of this angle when the wearer's head is in a natural posture, is determined.

The reference value Aref of the angle of inclination A can, for example, be determined in step c), by carrying out the following steps:

c1) at least one substantially profile image of the wearer's head 10 in a natural posture is captured, the wearer's head 10 comprising at least one profile indexing element positioned in such a way that it is identifiable on said substantially profile image of the face of the wearer, c2) on said substantially profile image, the image of this profile indexing element is identified, c3) a geometric characteristic of the image of this profile indexing element is determined, c4) the reference value Aref of said angle of inclination A is determined as a function of the geometric characteristic of the image determined in step c3).

Such a profile image is represented in FIG. 3.

In this FIG. 3, the wearer is in the natural posture. The Frankfurt plane is horizontal and the angle of inclination between the mean plane PM of the circles of the spectacle frame 30 of the wearer and the image capture plane PCI corresponding to the image capture in step a) is then equal to the looked-for reference value.

It is possible, to perform this profile image capture, either to ask the wearer to turn the head by approximately 90 degrees, or to move the image capture device in such a way that the image capture plane pivots by 90 degrees about a vertical axis.

In the latter case, the image capture device being moved in step c), it is necessary to know its position and its orientation in step c) relative to the position and the orientation of the image capture device during the substantially frontal image capture of step a).

An example is described here in which the facial image capture plane in step a) is substantially vertical.

Obviously, this facial image capture plane can be non-vertical.

In a more general case, means are provided for determining the orientation in a reference frame of the space of the device in order to determine the orientation of the device relative to two perpendicular horizontal axes. These means thus make it possible to determine a pitch and roll angle relative to each of these two axes.

Such means are known, for example, from the document U.S. Ser. No. 12/596,351.

Two profile indexing elements 23, 24 are provided here on the accessory 20, as described previously.

In step c1) the wearer is placed in a natural position. For this, whether he or she is asked to pivot the head relative to the image capture device or whether the image capture device is pivoted relative to him or her, he or she is seated or standing, head straight, and looking into the far distance, in a direction approximately perpendicular to the optical axis of the image capture device.

The wearer looks, for example, to the horizon if this is possible. As a variant, he or she looks at a point situated more than two meters away from him or her, preferably situated more than 5 meters straight in front.

This point may be embodied by a target on a wall situated in front of the wearer.

Furthermore, as mentioned previously, in a substantially profile image the image capture plane PCI of the image capture device forms an angle of between +10 and −10 degrees about the axis AV with the sagittal plane PS of the wearer's head. Preferentially, the sagittal plane PS of the wearer's head is parallel to the image capture plane.

In step c2), on said substantially profile image, the image of each profile indexing element 23, 24 is identified. The processing of the profile image carried out to identify these profile indexing elements will be detailed later.

In step c2), the coordinates, within a reference frame of the plane of the image for example attached to a corner of this image, of the profile indexing elements 23, 24 are determined; for example, the coordinates of their centers are determined, followed by the coordinates (X, Y) of the segment linking their centers.

The reference value Aref of the angle of inclination A between the mean plane of the frames PM and the image capture plane PCI in step a) is then equal to arctan(Y/X). Preferentially, the image capture device is a video camera and a series of substantially profile images of the wearer's head is captured.

The video image capture device preferentially captures between 1 and 30 images per second, preferentially between 5 and 20 images per second, for example 15 images per second.

All the captured images are not used to determine the looked-for geometric/physiognomic parameter, but some of them make it possible to refine the settings of the image capture device, as explained hereinbelow, so as to improve the brightness and the sharpness of the subsequently captured images of the indexing elements of the accessory 20, so as to ensure their precise identification.

Steps c2) to c4) are then repeated for a plurality of images of the series and the reference value Aref of the angle of inclination A is determined as the average value of the reference values determined for each image.

The reference value obtained is then more accurate.

Preferentially, a first arithmetic average of all the reference values determined from the series of images is calculated and a standard deviation of each reference value is determined relative to this first average.

From the set of the reference values considered, those for which the deviation with the first calculated average is greater than a threshold deviation determined as a function of the standard deviation are then eliminated. The threshold deviation is, for example, equal to twice the calculated standard deviation.

The arithmetic average of the remaining reference values is then calculated and this second calculated average is identified at the looked-for reference average value.

As a variant, as for the frontal indexing elements, the profile indexing element or elements can be noteworthy anatomical elements of the wearer's head.

Also as a variant, the reference value of the angle of inclination can be determined in step c) by an inclinometer.

As yet another variant, this reference value can be predetermined and stored in a table, for a given wearer. It can then be simply extracted from this database for the implementation of step c).

Step d)

The looked-for geometric/physiognomic parameter is finally determined on the basis of the substantially frontal image captured in step a) as a function of the difference between the measured value Am and the reference value Aref of the angle of inclination A.

In practice, the geometric/physiognomic parameter is determined either by measuring on the captured image the quantity corresponding to the looked-for parameter in the image capture plane and by taking into account a scale factor that is a function of the distance between the head and the image capture plane PCI and a function of the inclination of the head relative to this image capture plane. For example, the height of the pupils relative to the bottom edge of the frame or the interpupillary distance is measured, and the measured quantity is multiplied by the scale factor.

It is then possible, either to correct the measured quantity as a function of the reference value of the angle of inclination, or to correct the determined geometric/physiognomic parameter as a function of this reference value, in order to obtain the geometric/physiognomic parameter corresponding to the natural posture of the wearer.

For example, in the case of the determination of the height Hp of the pupils of the eyes, the corresponding distance, represented in FIG. 2, is measured on the substantially frontal image captured in step a). This distance can be determined automatically by a processing of the image identifying the position of the images of the corneal reflections of a light source placed in proximity to the image capture device as the position of the pupils and the image of the bottom edge of the frame.

The reference value of the angle of inclination is then introduced into the conventional calculation of the height of the pupils.

More specifically, the height Hp of the pupils is, for example, determined from the substantially frontal image captured in step a) according to a known method described in the document U.S. Ser. No. 12/596,351.

The height of the pupils Hpn in a natural posture is then calculated as a function of the known distance dCRO between the center of rotation of the eye and the lens of the corresponding frame by the formula: Hpn=Hp+dCRO*tan(Aref−Am), where tan is the tangent function and the angle convention is such that the angles cross when the wearer leans the head forward.

As explained previously, the steps b1) and c2) of the method rely respectively on the identification of the image of at least one frontal indexing element on the substantially frontal image captured in step a) and on the identification of the image of at least one profile indexing element on the substantially profile image captured in step c1).

In order to ensure that the identification of these images is possible, the method according to the invention also proposes ensuring the capture of a frontal and/or profile image that can be used for the image processing that has to be carried out during the abovementioned steps.

To this end, it should preferably be checked that two simultaneous conditions are satisfied for each captured image, namely that the brightness of at least a portion of the image containing the image of the indexing elements is sufficient, and that this portion of the image is sharp.

These two settings are particularly important in the case of the profile image capture and will be described hereinbelow in this context.

They nevertheless apply in the same way to the captured frontal images.

Preliminary Steps: Setting the Brightness and/or Setting the Sharpness of the Image Rough Brightness Setting Provision can be made to first of all make a first rough and rapid setting of the acquisition parameters of the image capture device, by the following steps, represented in the blocks 100, 201, 202 of FIG. 1:

p1) a preliminary substantially profile image of the wearer's head is captured (block 100), p2) a measured value of the average brightness of at least one reduced area of this preliminary image is determined, this reduced area being adapted to cover at least a portion of the image of the wearer's head (block 201), p3) the setting parameter of the optical acquisition conditions of the image capture device is adjusted roughly as a function of this measured value so as to improve the contrast of the captured image of the wearer's head (block 202), p4) the setting parameter of the optical acquisition conditions obtained in step p3) is used to adjust the optical conditions of the subsequent image captures, notably in step c1) (return to block 100).

The reduced area of the image captured in step p1) used in step p2) is, for example, a left or right lateral area of the image depending on whether the projection of the accessory is situated to the left or to the right of the profile image. It is, for example in the image I3 of FIG. 3, the right half I4 of this image.

This reduced area is, for example, a central area I2 (FIG. 2) of the image I1 when the image is captured from the front.

In step p2), an average luminance or chrominance of this reduced area of the image is determined and, in step p3):

the deviation between the measured value determined in step p2) and a target brightness value is determined, this deviation is compared with a predetermined maximum value of this deviation, and based on this comparison, in step p3), the setting parameter of the optical acquisition conditions of the image capture device is adjusted so as to make said measured value tend toward said target brightness value. This adjustment is detailed hereinbelow in the part relating to the fine brightness setting.

If the setting parameter of the optical acquisition conditions of the image capture device has been modified, steps p1) to p4) are repeated (blocks 100, 201, 202).

If the average brightness on the lateral area of the image assessed in step p2) is satisfactory, that is to say the deviation between the measured value determined in step p2) and a target brightness value is less than the predetermined maximum deviation value, a setting of the sharpness of the image and a fine setting of the brightness can then be made.

The rough brightness setting step is optional and it is equally possible to directly make the sharpness and brightness settings explained hereinbelow.

The first steps of these two settings consist of a capture of a substantially profile image of the wearer's head (block 100 of FIG. 1), and a detection of the position of the indexing elements (blocks 203 and 301 of the figure), which here form brightness calibration elements and sharpness assessment elements.

Identification of the Indexing Elements: Determining their Position

In practice, a series of images is captured at regular time intervals (block 100 of FIG. 1). The image capture parameters of the capture device are modified according to the steps described hereinbelow as the images are captured and processed.

The captured images are here, for example, black and white images in which each pixel exhibits a given luminance.

As a variant, it is also possible to envisage capturing an image in color, that is to say in which each pixel contains luminance and chrominance information, and converting this color image into a gray-tone image.

For this, the image captured in (R, G, B) coding comprising red R, green G and blue B components is converted in a known manner into coordinates (Y, U, V) comprising luminance Y and chrominance U, V components. The luminance of each pixel is obtained by the formula:

$$Y=0.299*R+0.587*G+0.114*B.$$

The image of each indexing element therefore exhibits, in the captured image, an arrangement of light and dark areas corresponding to the images of the light and dark areas of the corresponding indexing element, that is to say a determined brightness distribution. This brightness distribution can be a luminance or chrominance distribution.

A step of re-sampling of the captured image, intended to reduce the total number of pixels in the image, is preferentially carried out first of all.

The subsequent image processing steps described hereinbelow are then faster, because the computation times are reduced with the reduction in the number of pixels in the image.

The re-sampling coefficient is, for example, between 1.5 and 3. It is for example equal to 2.

As a variant, it is possible to use the non-re-sampled captured image.

To determine the position of the image of each indexing element on the captured image, a convolution step s) is carried out on at least a portion of the captured image via a detection matrix reproducing the expected brightness distribution of the image of one of the indexing elements.

Here, the two profile indexing elements 23, 24 are not identified during the image processing described because they exhibit a luminance distribution that is different from that of the frontal calibration elements 21D, 21G, 22H, 22B.

In practice, here the light and dark areas are reversed on the profile indexing elements. The detection matrix used to determine the position of the frontal indexing elements is not therefore suitable for determining the profile indexing elements. This brightness distribution can be a luminance or chrominance distribution depending on the type of indexing element used, as explained previously.

Here, given the arrangement of the dark ZS and light ZC areas of each profile indexing element 23, 24, in the convolution step s), said detection matrix takes the form:

$$\begin{vmatrix} m & -m \\ -m & m \end{vmatrix}$$

Each element m of the detection matrix is a submatrix comprising a number of rows and a number of columns such that the convolution matrix has dimensions less than or equal to the corresponding dimensions in pixels of the image of one of the indexing elements.

For example, in the case of the profile indexing elements, if the indexing element in reality measures 6 millimeters in length by 6 millimeters in height and its image initially extends on the captured image over 12 pixels in length and 12 pixels in height, after re-sampling, it extends over 6 pixels in length and 6 pixels in height.

Each dark area ZS and each light area ZC of the indexing element therefore extends over 3 pixels in length and 3 pixels in height.

Each element m of the detection matrix then comprises, for example, 3 columns and 3 rows.

In the example described here, the brightness of each dark or light area is uniform, the coefficients of each element m of the detection matrix are then preferably all equal.

Furthermore, the sum of the coefficients of each element m of the detection matrix is preferentially equal to ½ in order to avoid saturation phenomena during the convolution.

In the example given here, the matrix m takes the form:

$$m = 1/18 * \begin{vmatrix} 1 & 1 & 1 \\ 1 & 1 & 1 \\ 1 & 1 & 1 \end{vmatrix}$$

The convolution of the captured image by this detection matrix is, for example, carried out for the totality of the image. This makes it possible to identify the image of each indexing element, without a priori knowledge of the position of the latter in the image, which is notably the case during the convolution of the first image of a series of images.

It would, however, also be possible to envisage carrying out, before this convolution step, a step of approximately estimating the position of the indexing elements.

It is also possible to perform a tracking of the position of the indexing elements: from the position of an indexing element on a given image of the wearer's head, an approximate position of this indexing element on the next image can be estimated, for example as a function of the time interval between two image captures and the average speed of displacement of the head of a wearer.

Only a portion of the next captured image, situated in the region determined previously, is then convoluted by the detection matrix. The computation is thus faster.

In the example described, the region of the image convoluted by the detection matrix comprises groups of pixels belonging to the indexing elements and other groups of pixels which do not belong to the indexing elements.

It is then possible to perform a step t) of reinforcing the contrast of the image convoluted in step s), during which the luminance of the groups of pixels belonging to the indexing elements is increased. For this, at least a portion of the captured image is convoluted by a reinforcement matrix whose dimensions are less than or equal to the corresponding dimensions in pixels of the image of an indexing element and whose coefficients increase the edges toward the center of the reinforcement matrix.

The size of this reinforcement matrix depends on the size of the image of the calibration element, and therefore on the re-sampling coefficient.

The convolution of the image obtained in step s) by this reinforcement matrix makes it possible to increase the luminance of the pixels situated in the areas where the luminance follows the distribution expected for the image of an indexing element in order to facilitate their detection.

The determination of the position of the indexing elements is thus more accurate.

A step u) of searching for isolated maxima is then performed on the image obtained in step t), or on the image obtained in step s) if the convolution by the contrast reinforcement matrix is not carried out.

More specifically, in step u), groups of pixels exhibiting an isolated brightness peak and having a size less than the size of the brightness calibration element in all the directions are detected.

For this, on the image obtained in step s) or t), the pixels for which the brightness is greater than a predetermined brightness threshold value are identified.

The predetermined brightness threshold value can obviously be a luminance or chrominance threshold value depending on the type of indexing element used.

An algorithm for filling an isolation matrix centered on each identified pixel, is then used. This algorithm fills the matrix with the brightness values of the pixels adjacent to said identified pixel if this brightness is greater than said threshold value.

The size of the isolation matrix is chosen as a function of the looked-for image size of the indexing element.

If the isolation matrix remains empty along its edges, this means that the group of pixels situated around the identified pixel corresponds to an isolated maximum.

A first selection is, for example, performed among all the groups of pixels identified in step u), by retaining only the ten groups with the greatest brightness.

A step v) is then carried out to select at least two of the groups of pixels which exhibit an isolated brightness peak detected in step u) and exhibiting the highest probability of being associated with the image of two of the indexing elements of the accessory, namely at least two groups of pixels for which the deviation is reduced between:
- a measured distance between these two groups and a reference distance, and/or
- an angle measured between the straight line passing through these two groups and a reference direction and a reference angle, and/or
- the brightness measured in the vicinity of these two groups and a reference brightness, and/or
- the brightness difference between two points of predetermined relative positions relative to each group of pixels and a reference brightness difference.

For this, all the pairs of groups of pixels present in the image in a given direction are determined, for example by considering a first group of pixels and each other group of pixels situated to the left or to the right of this first group, or above or below this first group.

An overall score is assigned to each pair of groups of pixels so as to quantify their resemblance with the image of a given pair of indexing elements of the accessory.

The overall score assigned to each pair is determined as a function of the comparison of geometric and brightness characteristics of the groups of pixels with the expected characteristics of the image of the pair of indexing elements considered.

For example, the distance measured on the image between the two groups of this pair and the distance expected between the images of the two indexing elements 23, 24 are compared, and a first intermediate score is assigned to the pairs considered which becomes all the greater as the deviation between these two distances decreases. The distance expected between the images of the two indexing elements is determined as a function of a scale factor that notably takes into account the re-sampling of the image.

The angle measured on the image between the straight line passing through these two groups and a direction representing, for example, the image of a horizontal straight line and the angle expected between the straight line linking the images of the two indexing elements and the image of a horizontal plane are compared. A second intermediate score, that becomes all the greater as the deviation between these two angles decreases, is then assigned to the pair considered.

The brightness measured in the vicinity of these two groups and a reference brightness determined as a function of the preceding image captures are also compared.

When a series of images is captured, it can be assumed that the brightness values measured on two successive images are close. Thus, the pair considered is assigned a third intermediate score that becomes all the greater as the abovementioned brightness deviation decreases.

Finally, it is possible, here, for example, to compare, for each group of pixels of said pair, a reference brightness difference and the brightness difference between two points of relative positions chosen such that they are situated in two adjacent quadrants and/or in two diagonally opposite quadrants of the image of the indexing element in the case where this group of pixels is the image of an indexing element.

It is also possible to exclude from the selection made in step v) the pairs of two groups of pixels for which the deviation between a distance measured between these two groups and a reference distance, and/or an angle measured between the straight line passing through these two groups and a reference direction and a reference angle, and/or the brightness measured in the vicinity of these two groups and a reference brightness and/or the brightness difference between two points of relative positions relative to each group of predetermined pixels and a reference brightness difference is greater than a threshold value.

The overall score for each pair is, for example, obtained by multiplying all the intermediate scores assigned to this pair. As a variant, these intermediate scores can be weighted according to the importance or the reliability of the criterion considered.

The pair of groups of pixels that exhibits the best overall score is identified with the looked-for pair of images of the indexing elements.

In the case where this determination of the positions of the images of the indexing elements is carried out on a re-sampled image, it is possible to envisage repeating, on the non-re-sampled image, the step of convolution by a detection matrix reproducing the expected brightness distribution of the image of the indexing element, in a reduced area of the non-re-sampled image centered around the position of the non-re-sampled image corresponding to each position determined for the indexing elements on the re-sampled image.

The size of the detection matrix used in this step is then adapted to the non-re-sampled image.

Sharpness Setting

This setting can be carried out after or before the rough and/or fine brightness setting.

In the example of FIG. 1, it is carried out after the rough brightness setting and before its fine setting.

This setting comprises, after a step h) of capture of a substantially profile image of the wearer's head, and a step i) of determining the position of the image of at least one of the profile indexing elements on this image captured in step h), according to the method described previously, the following steps:

j) a sharpness parameter representative of the sharpness of the image of this profile indexing element on this image is determined, k) this sharpness parameter is compared with a predetermined sharpness threshold value, l) the image acquisition focal distance of said image capture device is modified as a function of the difference between the sharpness parameter determined in step j) and said sharpness threshold value, so as to improve the sharpness of the image of the profile indexing element.

In step j), it is possible to use the image captured in step h) or the image convoluted by the detection matrix obtained in step i) in determining the position of the image of the indexing element.

Steps j) and k) form a sharpness test represented by the block 204 in FIG. 1.

In step j), the size or the brightness of the image of a particular point of the profile indexing element is determined and said sharpness parameter is deduced therefrom.

For example, the size and the form of the spot representing the center of the indexing element is determined according to the position of this indexing element determined in the preceding step.

The larger this size becomes, the more blurred the image becomes.

Similarly, the more blurred the image becomes, the more the brightness of the center of the indexing element decreases.

Thus, if the size of the spot representing the center of the indexing element is greater than a size threshold value or if the brightness of this spot is less than 50% of the luminance peak, the sharpness of the image is unsatisfactory and, in step l), a program for adjusting the acquisition focal distance of the image capture device is initiated (block 300 of FIG. 1).

This program comprises the following steps: initialization (block 300), detection of the focal distance corresponding to a maximum sharpness of the indexing elements (block 302), changing of the increment and of the direction of modification of the focal distance (block 303), adjustment of the acquisition focal distance (block 304).

The acquisition focal distance can, for example, be set between 50 and 70 centimeters.

When the algorithm is started up, the following initializations are performed:

the focal distance of the image capture device is set to its minimum value, called FocusMin, equal to 50 centimeters in the example, the increment of the focal distance of the image capture device, called DeltaFocus and equal to the deviation between two successive values of the focal distance tested by the program, is set to a positive initial value that is high relative to the extent of the range, for example equal to a tenth of the deviation between the extreme values of the focal distance that can be accessed for this image capture device, here 2 centimeters for example, the direction of modification of the focal distance, called SensFocus, is initialized in the direction of increasing this focal distance.

Conversely, it would be possible to envisage having the focal distance of the image capture device being set to its maximum value, and the direction of modification of the focal distance initially being the direction of reducing this distance.

In the step of detecting the focal distance that corresponds to a maximum sharpness, the focal distance of the image capture device is incremented, and steps j) and k) described previously are repeated, by using, in step k), a predetermined maximum threshold value of the sharpness of the image.

If the measured size or brightness value on the image is greater than said maximum sharpness threshold value, the program is configured to restart the acquisition of a new image (block 100).

In this case, since the external autofocus program is initiated, the rough brightness setting steps are not performed.

The position of the indexing elements is then determined (block 301) and the step of detecting the maximum sharpness of the indexing elements is repeated.

If the size or brightness value measured on the image is less than said maximum sharpness threshold value, the focal distance corresponding to the maximum sharpness of the indexing elements is exceeded.

The program then performs a step of changing the increment and the direction of modification of the focal distance:
- the DeltaFocus increment is reduced, for example divided by 2,
- the direction of modification of the focal distance SensFocus is reversed.

The focal distance is then modified by reducing the focal distance by the new increment value.

After the program for setting the focal distance is started up, the image acquisition and processing steps described previously are repeated (blocks 100, 101, 301, 302, 303, 304) until the DeltaFocus increment is less than a predetermined value.

This predetermined value is, for example, reached when the difference between two successive steps is less than 10% of the initial increment value.

As a variant, in the step of detecting the maximum sharpness, for each image captured in succession with a focal distance value increased by the DeltaFocus increment, the size or the brightness of the image of a particular point of the profile indexing element is determined and the corresponding sharpness parameter is deduced therefrom. The program compares, for each increment of the focal distance, the value of the sharpness parameter with the value of the sharpness parameter determined for the preceding increment of the focal distance. The value of the sharpness parameter varies continuously so as to tend toward a value corresponding to a maximum sharpness. When the direction of variation of this parameter is reversed, the focal distance corresponding to the maximum sharpness is exceeded.

The following steps are unchanged: the program then performs a step of changing the increment and the direction of modification of the focal distance, and then the step of detecting the maximum sharpness is repeated with these initial values.

The maximum is detected with sufficient accuracy when the value of the increment becomes less than an increment threshold. When this increment value is reached, the program retains the focal distance value corresponding to the reversal of the variation of the sharpness parameter obtained with this increment as focal distance value for the subsequent image captures and the program is stopped.

Preferentially, the sharpness setting is performed after the rough brightness setting, and the profile image of the wearer's head captured in step h) is captured with the setting parameter of the optical acquisition conditions modified in step p3).

Preferentially, in the next step c1), the profile image of the wearer's head is captured with the image acquisition focal distance modified in step l).

Fine Brightness Setting

This setting is, for example, performed after the setting of the sharpness of the indexing elements.

After the program for setting the acquisition focal distance is stopped, the next image captured has a satisfactory rough brightness setting and a satisfactory sharpness setting.

A fine setting of the brightness of the images of the indexing elements is then carried out (blocks 205, 206 of FIG. 1).

In order to allow for the fine brightness setting, the accessory 20 comprises at least one brightness calibration index comprising at least two contrasted areas which can be seen on said profile image of the wearer.

Here, the brightness calibration elements are merged with the indexing elements described previously. The accessory therefore comprises four brightness calibration indexes which can be seen in a substantially frontal image which are the frontal indexing elements 21D, 21G, 22H, 22B and two calibration indexes which can be seen in a right or left substantially profile image which are the profile indexing elements 23, 24. Advantageously, the method comprises the following steps, prior to step c1), to ensure the capture of a substantially profile image of acceptable brightness:

e) a substantially profile image of the wearer's head is captured (block 100 of FIG. 1), f) a measured value of the brightness of at least a portion of the image of the calibration element captured in step e) is determined (block 205 of FIG. 1), said image here being the image of one of the indexing elements, g) a setting parameter of the optical image acquisition conditions of said image capture device is modified as a function of this measured value, so as to improve the contrast of the image of the contrasted areas of the calibration element (block 206 of FIG. 1).

Preferentially, in step e), the substantially profile image of the wearer's head is captured with the setting parameter of the optical acquisition conditions modified in step l).

As previously, the brightness can be a luminance and/or chrominance value depending on the indexing elements used.

In step f), the position of the indexing elements is identified as described above, or the positions identified in a preceding step are used. Once the position of the indexing elements is determined, a measured value of the brightness, luminance and/or chrominance, of at least a portion of the image of this brightness indexing element is determined.

The portion of the image of the brightness calibration element for which a measured value of the brightness is determined is called the measurement area hereinbelow. It is, for example, situated straddling said two contrasted areas of the calibration element.

The measured brightness value is an average value over all of the measurement area.

Here, this measurement is performed in an area straddling the four contrasted areas, preferably centered on the center of the calibration element.

In step g), the following substeps are performed:

g1) the deviation between the brightness value determined in step f) and a target brightness value is determined, g2) this deviation is compared with a predetermined maximum value of this deviation, g3) based on this comparison, the setting parameter of the optical acquisition conditions of the image capture device is modified so as to make said measured value tend toward said target brightness value.

The target brightness value is predetermined by a prior calibration step. It can, for example, be determined from a first image captured in optimum brightness conditions or be determined from an average value of the measured value of the brightness over the images that can be used.

In practice, if this deviation is greater than a predetermined maximum value of this deviation, the modification of the setting parameter of the optical acquisition conditions of the image capture device is, for example, equal to the difference between the target brightness value and said measured value of the brightness divided by said predetermined maximum value of the deviation between this target brightness value and this measured value.

If this deviation is less than a predetermined maximum value of this deviation, the modification of the setting parameter is zero and it is possible to go directly to checking the sharpness, if the latter is performed after this step, or to determining the geometric/physiognomic parameter (block 400 of FIG. 1).

Said predetermined maximum value of the deviation between the target value and the measured brightness value depends, for example, on the number of setting steps for the setting parameter of the optical acquisition conditions of the image capture device. The more setting steps this setting parameter has, the greater the predetermined maximum value of the deviation will be, in order to nevertheless allow for a rapid setting of this parameter.

The modification of the setting parameter can advantageously depend on the measured brightness value, on the target value and on the current value of the setting parameter.

The link between the brightness and the setting parameter is not necessarily linear on the cameras. For example, a small modification of the setting parameter when the image is saturated or underexposed can still have no visible effect.

Thus, it may be advantageous to vary the predetermined maximum value of the deviation as a function of the current value of the setting parameter.

The setting parameter of the optical acquisition conditions of the image capture device is an aperture and/or gain and/or exposure time parameter.

In practice, the image capture device is, for example, a video camera operating in the interlaced PAL format. The initial size of the image, before re-sampling, is, for example, 720×576 pixels.

The brightness parameter "bright" of the camera is then adjusted.

The brightness parameter is not a physical parameter of the camera, but a setpoint. The camera is, for example, used in semi-automatic setting mode. Based on the desired brightness parameter, the camera then automatically adjusts the following three hardware parameters:
- iris or aperture or diaphragm,
- gain,
- pause or "shutter" time.

In step c1), the substantially profile image of the wearer's head is preferentially captured with the setting parameter of the optical acquisition conditions modified in step g).

As a variant, if the sharpness setting is performed after the brightness setting, the profile image of the wearer's head captured in step h) is captured with the setting parameter of the optical acquisition conditions modified in step g).

Thus, the step of determining the reference value of the angle of inclination can be performed from a substantially profile image having a brightness and a sharpness suitable for obtaining an accurate result and the step of determining the looked-for geometric/physiognomic parameter (block 400) is performed on a substantially frontal image whose brightness and sharpness are also satisfactory.

The steps of identifying the position of the images of the indexes of the accessory, of setting the sharpness and the brightness, can be implemented equally for the profile indexing elements and for the frontal indexing elements. Thus, they are applicable to the substantially profile image to allow for the determination of the reference value of the angle of inclination, and to the frontal image to allow for the determination of the measured value of the angle.

The invention claimed is:

1. A method for determining at least one geometric/physiognomic parameter associated with the mounting of an ophthalmic lens in a spectacle frame (30) intended to be worn by a wearer, in a natural posture of the wearer's head in which a Frankfurt plane (PF) of the wearer's head is substantially horizontal, comprising the following steps:
    a) capturing at least one substantially frontal image of the wearer's head (10) with an image capture device,
    b) determining a measured value (Am) of an angle of inclination (A) of the wearer's head (10) during the capture of the substantially frontal image, which depends on the inclination of the wearer's head about a main axis perpendicular to a sagittal plane (PS) of the wearer's head,
    c) determining a reference value (Aref) of said angle of inclination (A) corresponding to a natural posture of the wearer's head (10), by carrying out the following steps:
        c1) capturing at least one substantially profile image of the wearer's head in the natural posture with at least one profile indexing element (23, 24) positioned on the wearer's head (10), where said at least one substantially profile image includes an image of the at least one profile indexing element (23, 24) identifiable on the wearer's head,
        c2) identifying, on said substantially profile image, the image of the at least one profile indexing element (23, 24),
        c3) determining a geometric characteristic of the image of this profile indexing element, and
        c4) determining said reference value (Aref) of said angle of inclination (A) as a function of said geometric characteristic determined in step c3), and
    d) determining said looked-for geometric/physiognomic parameter on the basis of the substantially frontal image captured and as a function of the difference between said measured value (Am) of the angle of inclination (A) determined in step b) and said reference value (Aref) of said angle of inclination (A) determined in step c).

2. The method as claimed in claim 1, whereby, in step b), the angle of inclination (A) is the angle formed between a plane (PM) integral with the wearer's head (10) and an image capture plane (PCI) associated with the capture of said substantially frontal image.

3. The method as claimed in claim 2, whereby said plane (PM) integral with the wearer's head (10) is a mean plane (PM) of the circles of the spectacle frame (30) positioned on this wearer's head.

4. The method as claimed in claim 1, whereby the wearer's head comprises at least one frontal indexing element (21D, 21G, 22H, 22B) positioned in such a way that it is identifiable on said substantially frontal image of the face of the wearer, and, in step b):
    b1) the image of the frontal indexing element is identified on this substantially frontal image,
    b2) a geometric characteristic of the image of this frontal indexing element is determined,
    b3) said measured value (Am) of the angle of inclination (A) associated with the substantially frontal image is determined as a function of the geometric characteristic determined in step b2).

5. The method as claimed in claim 1, whereby steps c1) to c4) are repeated and the reference value (Aref) of the angle of inclination (A) is determined as the average value of the reference values determined in a plurality of steps c4) carried out.

6. The method as claimed in claim 4, whereby said at least one profile indexing element (23, 24) and said at least one frontal indexing element (21D, 21G, 22H, 22B) are positioned in such a way to be identifiable on said substantially frontal image of the face of the wearer, are situated on an accessory (20) positioned on the wearer's head (10).

7. The method as claimed in claim 1, whereby, the wearer's head (10) also comprising at least one brightness calibration indexer (23, 24) comprising at least two contrasted areas, visible in said profile image of the wearer, the method also comprises the following steps, prior to step c):
   e) a first substantially profile image of the wearer's head is captured,
   f) a measured value of the brightness of at least a portion of the image of the calibration element captured in step e) is determined,
   g) a setting parameter of the optical image acquisition conditions of said image capture device is modified as a function of this measured value, so as to improve the contrast of the image of the contrasted areas of the calibration element.

8. The method as claimed in claim 7, whereby, in step g),
   g1) the deviation between the brightness value determined in step f) and a target brightness value is determined,
   g2) this deviation is compared with a predetermined maximum value of this deviation,
   g3) based on this comparison, the setting parameter of the optical acquisition conditions of the image capture device is modified so as to make said measured value tend toward said target brightness value.

9. The method as claimed in claim 7, whereby, in step c1), the substantially profile image of the wearer's head (10) is captured with the setting parameter of the optical acquisition conditions modified in step g).

10. The method as claimed in claim 1, also comprising the following steps, prior to step c):
    h) a first substantially profile image of the wearer's head (10) is captured,
    i) the position of the image of the profile indexing element (23, 24) on this image captured in step h) is determined,
    j) a sharpness parameter representative of the sharpness of the image of this profile indexing element on this image is determined,
    k) this sharpness parameter is compared with a predetermined sharpness threshold value,
    l) the image acquisition focal distance of said image capture device is modified as a function of the difference between the sharpness parameter determined in step j) and said sharpness threshold value, so as to improve the sharpness of the image of the profile indexing element (23, 24).

11. The method as claimed in claim 7, also comprising the following steps, prior to step c):
    h) a first substantially profile image of the wearer's head (10) is captured,
    i) the position of the image of the profile indexing element (23, 24) on this image captured in step h) is determined,
    j) a sharpness parameter representative of the sharpness of the image of this profile indexing element on this image is determined,
    k) this sharpness parameter is compared with a predetermined sharpness threshold value,
    l) the image acquisition focal distance of said image capture device is modified as a function of the difference between the sharpness parameter determined in step j) and said sharpness threshold value, so as to improve the sharpness of the image of the profile indexing element (23, 24),
    whereby, in step h), the profile image of the wearer's head is captured with the setting parameter of the optical acquisition conditions modified in step g).

12. The method as claimed in claim 7, also comprising the following steps, prior to step c):
    h) a first substantially profile image of the wearer's head (10) is captured,
    i) the position of the image of the profile indexing element (23, 24) on this image captured in step h) is determined,
    j) a sharpness parameter representative of the sharpness of the image of this profile indexing element on this image is determined,
    k) this sharpness parameter is compared with a predetermined sharpness threshold value,
    l) the image acquisition focal distance of said image capture device is modified as a function of the difference between the sharpness parameter determined in step j) and said sharpness threshold value, so as to improve the sharpness of the image of the profile indexing element (23, 24),
    whereby, in step e), the profile image of the wearer's head is captured with the setting parameter of the optical acquisition conditions modified in step l).

13. The method as claimed in claim 10, whereby, in step c1), the profile image of the wearer's head is captured with the image acquisition focal distance modified in step l).

14. The method as claimed in claim 10, whereby, in step j), the size or the brightness of the image of a particular point of the profile indexing element (23, 24) is determined, and said sharpness parameter is deduced therefrom.

15. The method as claimed in claim 7, whereby said profile brightness calibration indexer (23, 24) is merged with the profile indexing element (23, 24).

16. The method as claimed in claim 1, wherein,
    the at least one substantially frontal image of the wearer's head (10) corresponds to an image for which an image capture plane (PCI) of said image capture device forms an angle about a vertical axis (AV) of the head with the frontal plane (PFr) of the wearer's head, the vertical axis (AV) of the head being defined as an intersection of the frontal plane (PFr) and of the sagittal plane (PS), and
    said measured value (Am) of the angle of inclination (A) of the wearer's head (10) is an angle, measured in the sagittal plane (PS), between i) the image capture plane (PCI), and ii) a plane integral with the wearer's head (10).

17. The method as claimed in claim 16, wherein,
    the plane integral with the wearer's head (10) is a mean plane (PM) of circles of the spectacle frame (30) worn by the wearer.

18. The method as claimed in claim 16, wherein,
    the plane integral with the wearer's head (10) is the frontal plane (PFr) of the wearer's head.

19. The method as claimed in claim 18, wherein,
    for the at least one substantially frontal image of the wearer's head (10) corresponding to the image for which the image capture plane (PCI) of said image capture device, the angle is between +20 and −20 degrees about the vertical axis (AV) of the head with the frontal plane (PFr) of the wearer's head.

* * * * *